(12) United States Patent
Kraft

(10) Patent No.: US 8,088,108 B2
(45) Date of Patent: Jan. 3, 2012

(54) RAPID LOCAL ANESTHESIA INJECTION CONE

(76) Inventor: Joseph Wayne Kraft, College Station, TX (US)

( * ) Notice: Subject to any disclaimer, the term of this patent is extended or adjusted under 35 U.S.C. 154(b) by 19 days.

(21) Appl. No.: 12/545,829

(22) Filed: Aug. 22, 2009

(65) Prior Publication Data

US 2011/0046556 A1    Feb. 24, 2011

(51) Int. Cl.
*A61M 5/00* (2006.01)
(52) U.S. Cl. .......................................... 604/173
(58) Field of Classification Search ............... 604/187, 604/173, 272–274
See application file for complete search history.

(56) References Cited

U.S. PATENT DOCUMENTS

| | | |
|---|---|---|
| 3,595,231 A | 7/1971 | Pistor |
| 3,941,126 A | 3/1976 | Dietrich |
| 4,586,490 A | 5/1986 | Katz |
| 5,997,509 A * | 12/1999 | Rosengart et al. ........ 604/164.01 |
| 6,518,255 B2 | 2/2003 | Rosengart |
| 6,537,242 B1 * | 3/2003 | Palmer ............................ 604/22 |
| 6,623,457 B1 | 9/2003 | Rosenberg |
| 6,716,190 B1 * | 4/2004 | Glines et al. .................... 604/70 |
| 6,743,211 B1 * | 6/2004 | Prausnitz et al. ............. 604/239 |
| 6,960,193 B2 | 11/2005 | Rosenberg |
| 7,047,070 B2 | 5/2006 | Wilkinson |
| 7,131,960 B2 | 11/2006 | Trautman |
| 7,479,134 B2 | 1/2009 | Olejnik |
| 2004/0186419 A1 | 9/2004 | Cho |
| 2005/0209565 A1 | 9/2005 | Yuzhakov |
| 2007/0270757 A1 | 11/2007 | Willis |
| 2008/0208134 A1 | 8/2008 | Tomono |
| 2009/0043250 A1 | 2/2009 | Gpnnelli |
| 2009/0054842 A1 | 2/2009 | Yeshurun |

* cited by examiner

*Primary Examiner* — Kevin C Sirmons
*Assistant Examiner* — Imani Hayman
(74) *Attorney, Agent, or Firm* — Jeffrey Furr, Esq.; Furr Law Firm

(57) ABSTRACT

This is a Local Anesthesia Injection Cone. It is made of a very simple cone shaped piece of clear plastic with a flange on the tip of the cone where a Luer lock syringe can attach. There are a multiple tiny hypodermic needles protruding from the base of the cone. The number of needles would be directly proportional to the diameter of the device. It would be available in many sizes identified by the diameter of the base of the cone.

8 Claims, 6 Drawing Sheets

RAPID LOCAL ANESTHESIA INJECTION CONE

CROSS-REFERENCES TO RELATED APPLICATIONS (IF ANY)

None

STATEMENT AS TO RIGHTS TO INVENTIONS MADE UNDER FEDERALLY-SPONSORED RESEARCH AND DEVELOPMENT (IF ANY)

None

BACKGROUND OF INVENTION

1. Field of the Invention

The present invention is directed to a Local Anesthesia Injection Cone, more particular to one that eases the delivery of anesthesia.

2. Background

Current techniques for establishing local skin anesthesia involve painful injections of local anesthetic into the periphery of the area to be anesthetized.

This painful procedure must unfortunately be performed very often in the outpatient setting during laceration repairs, IV insertions and other dermatologic procedures. This means that many times the already traumatized patient must undergo multiple painful injections of anesthesia over a prolonged period of several seconds to minutes. This traumatizes the patient with more than just the prolonged pain of the injections themselves, but also by the psychological trauma of seeing and feeling the needle repeatedly penetrating their skin. Many times after the pain of anesthesia infiltration there is still pain during the procedure because the clinician is not entirely sure of where the anesthesia begins and ends. This universally results in a negative patient experience, particularly in the pediatric population.

PRIOR ART

There exists prior art, Pat. No. 3,595,231 which is a device that consists in dividing a stream of the liquid to be injected into elementary streams feeding nipples connectable to injection needles. The device consists of a body, preferably constituted by a flat cylindrical disc, which comprises a main flow nipple connectable to an injection syringe, a plurality of secondary flow nipples and a network of internal ducts for dividing the main stream of the aforesaid liquid.

There is still room for improvement in the art.

SUMMARY OF THE INVENTION

This apparatus is a Local Anesthesia Injection Cone which is made of a very simple cone shaped piece of clear plastic with a flange on the tip of the cone where a Luer lock syringe can attach. Protruding from the round or oblong base of the cone are multiple tiny hypodermic needles. The number of needles would be directly proportional to the diameter of the device.

The device would be available in many sizes identified by the diameter of the base of the cone. These sizes could be denoted in, but not limited to, 1 cm increments. The shape of the base of the cone could be round or oblong depending on the shape of the area to be anesthetized. This would allow for significant individualization of the device to the specific area to be anesthetized.

BRIEF DESCRIPTION OF THE DRAWINGS

Without restricting the full scope of this invention, the preferred form of this invention is illustrated in the following drawings.

BRIEF DESCRIPTION OF THE PREFERRED EMBODIMENTS

Figure 1:
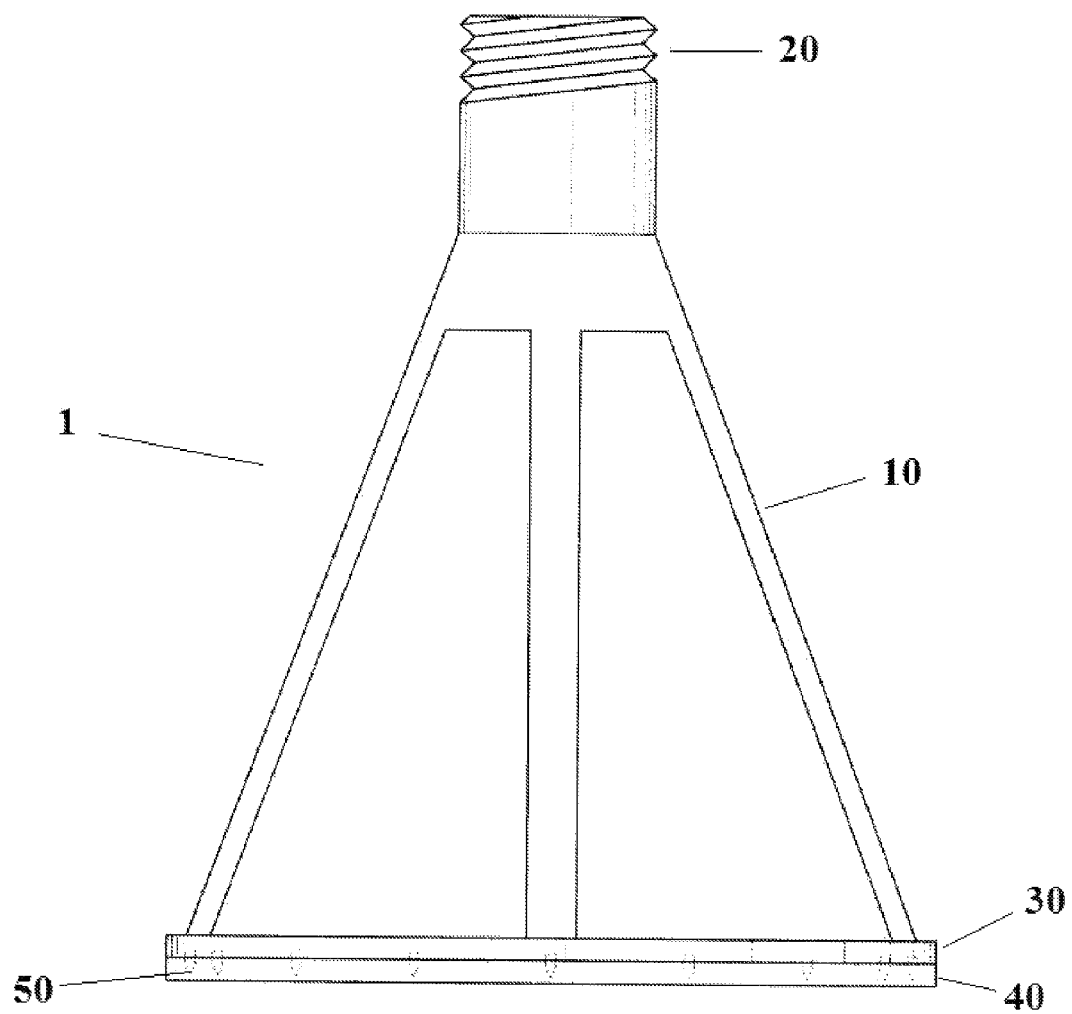
FIG. 1 is a side view of the Anesthesia Injection Cone.

There are a number of significant design features and improvements incorporated within the invention.

Current techniques for establishing local skin anesthesia involve painful injections of local anesthetic into the periphery of the area to be anesthetized.

The current invention is a Rapid Local Anesthesia Injection Ring that would significantly improve this unpleasant experience in many ways. The duration of the discomfort would be minimized to only 1-2 seconds. The psychological trauma would be limited greatly by there being no visible needle penetration. The area of anesthesia would be very well demarcated preventing painful inadvertent extension outside of the area of anesthesia. The total procedure time would be greatly reduced and the amount of user variability would be greatly controlled producing much more uniform and consistent resultant anesthesia.

As shown in FIGS. 1-5, the device 1 is a very simple cone shaped piece of clear plastic with a flange 20 on the tip of the cone 10 where a Luer lock syringe 100 can attach. Protruding from the base 30 of the cone 10 are multiple tiny hypodermic needles 50. The number of needles 50 would be directly proportional to the diameter of the device 1.

Figure 2:
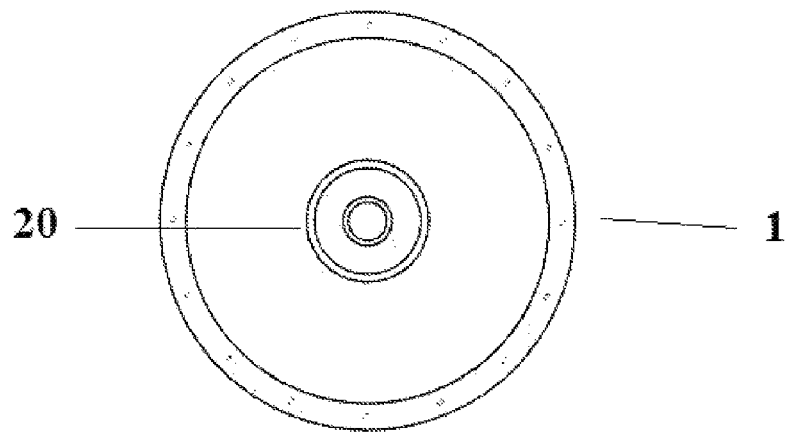
FIG. 2 is a top view of the device.
Figure 3:
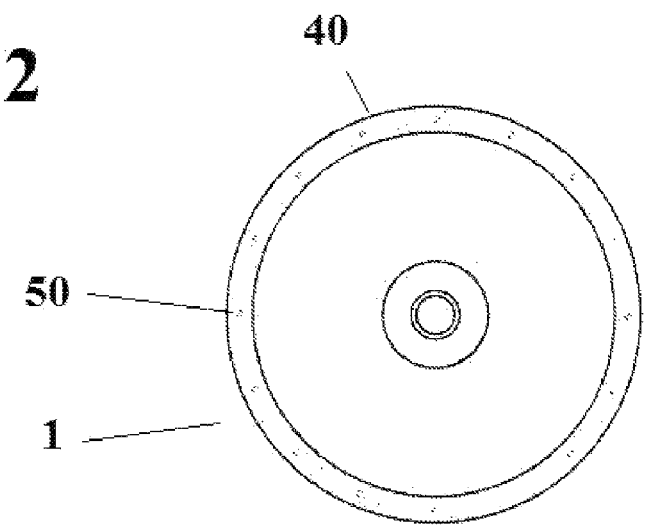
FIG. 3 is a bottom view of the device.
Figure 4:
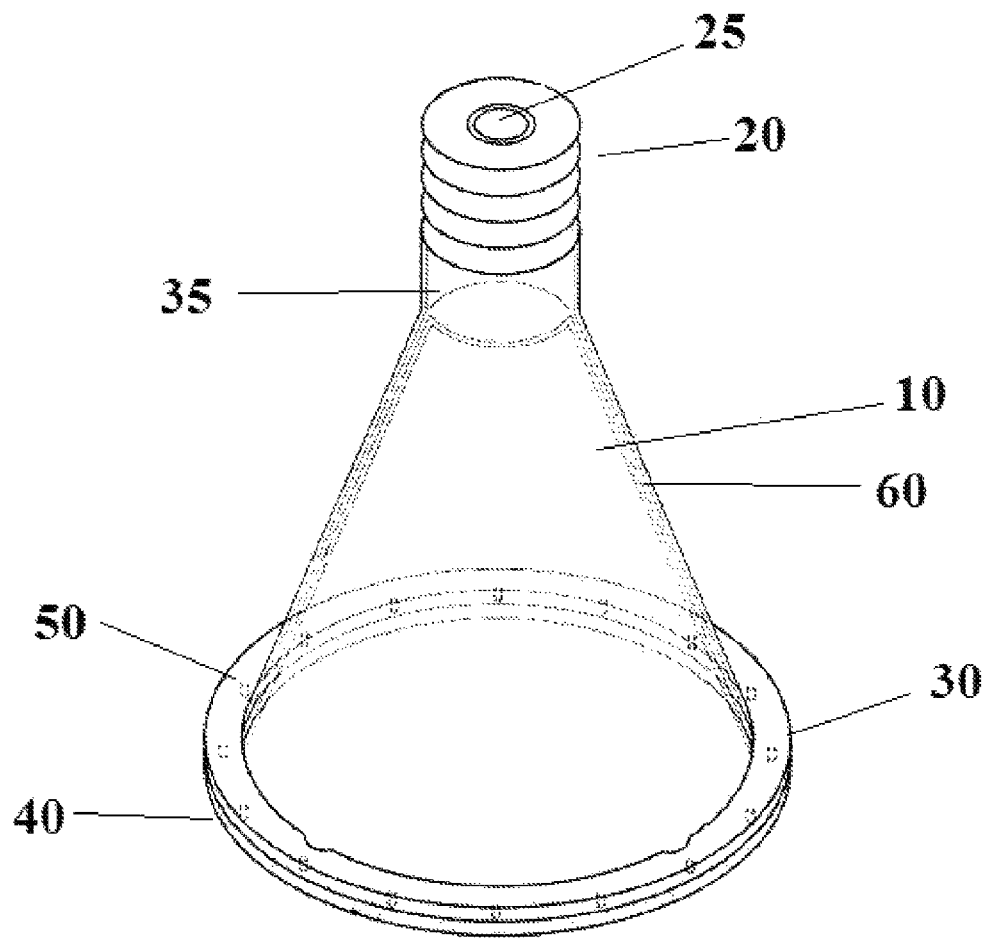
FIG. 4 is a front perspective of the device.
Figure 6:
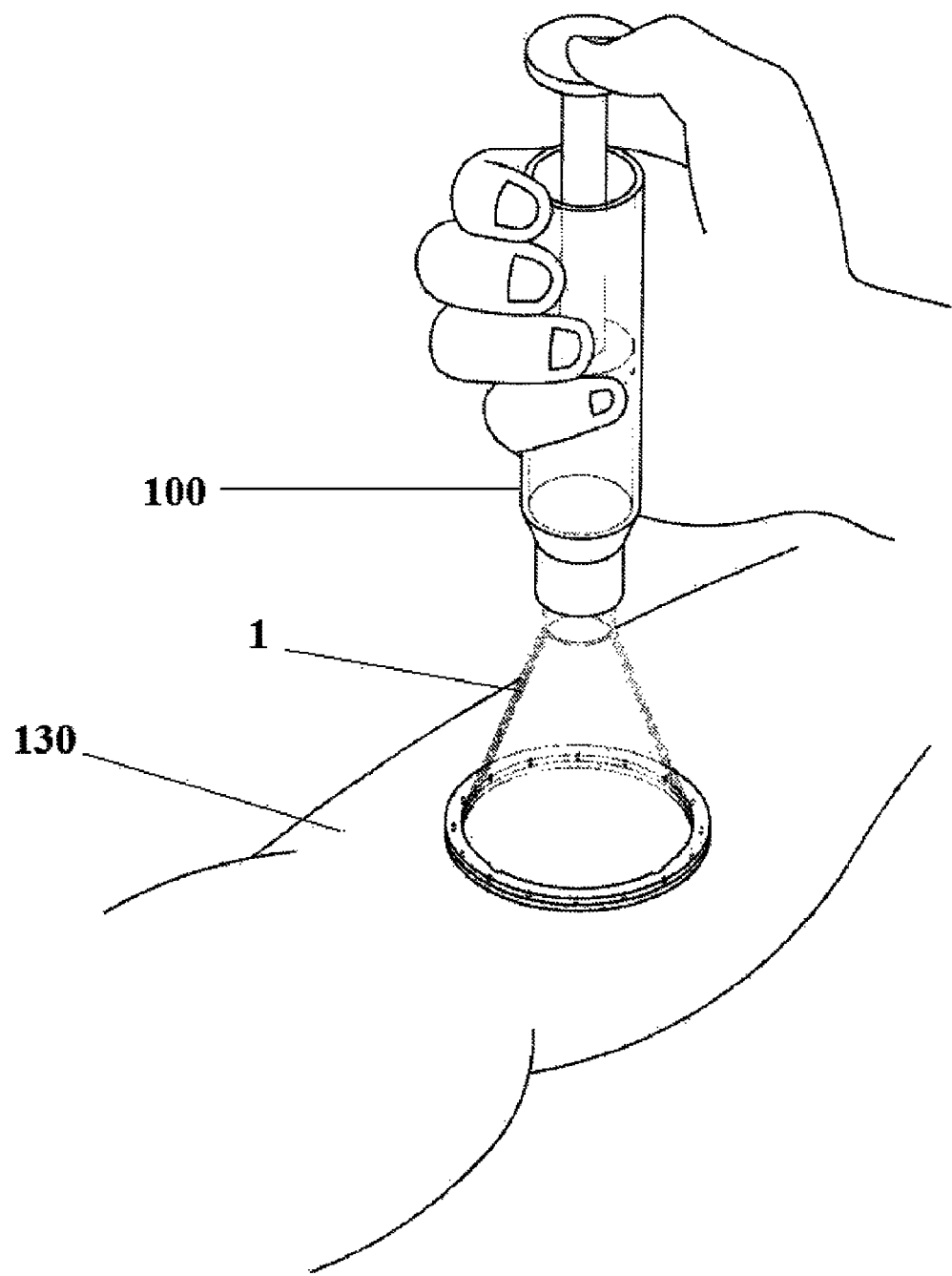
FIG. 6 displays the device being used.

As shown in FIGS. 2, 3 and 4, the device 1 is conical in shape with a conical body 10 with a chamber 55 at the top and a round or oblong base 30 at the bottom with hypodermic needles 50 protruding from the bottom of the base 30. The outside of the top of the device has a flange 20 and an opening 25 so that and flow device such as a Luer lock syringe 100 can be attached. In one embodiment, the Luer lock syringe 100 would be loaded with the anesthesia 120 for delivery to the device 1 as shown in FIG. 6. The anesthesia 120 flows from the delivery device such as a Luer lock syringe 100 to the chamber 55 to the conduits 60 to the hypodermic needles 50.

The device 1 came be made in many sizes identified by the diameter of the base 30 of the cone 10. These sizes could be denoted in, but not limited to, 1 cm increments. This would allow for significant individualization of the device determined by the size of the area that needs to be anesthetized.

Figure 5:
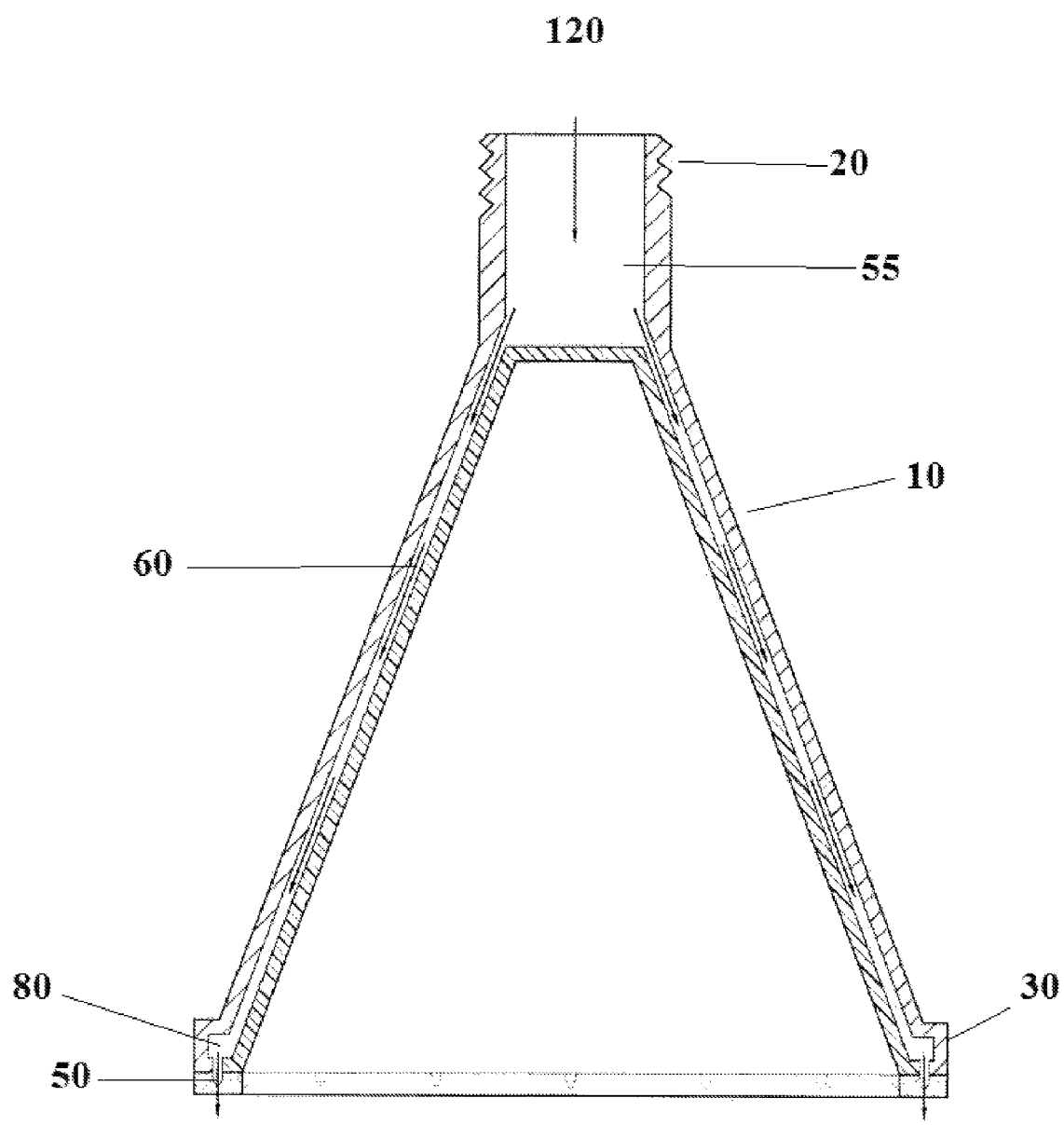
FIG. 5 is a cross-cut view showing anesthesia flow.

As shown in FIG. 5, the syringe 100 initially injects the anesthetic 120 into a small common chamber 55 that evenly feeds multiple conduits 60 in parallel fashion that carry equal amounts of the anesthetic to the short, very fine gauge needles which are mounted at a right angle to the base of the cone. The needles 50 would be distributed evenly around the base 30 of the cone 10 and in the preferred embodiment spaced approximately 5 mm apart to allow for complete circumferential anesthesia with a minimum of anesthetic.

The needles 50 protrude from the base 30 approximately 3-5 mm and are buried in approximately 5-8 mm of compressible rubber foam 40 in a ring or oblong shape where the length of the needles 50 is dependent on the compressibility factor of the foam ring 40.

FIG. 6 displays the device in use. The base 30 is placed against the skin 130. Force is applied down against the skin 130, exposing the hypodermic needles 50 from the foam ring 40 and allowing the hypodermic needles 50 to project into the skin 130 and the tissue underneath. The plunger of the Luer lock syringe 100 is pressed forcing the anesthesia 120 into the chamber 55 through the conduits 60 into the hypodermic needles 50 into tissue.

Figure 7:
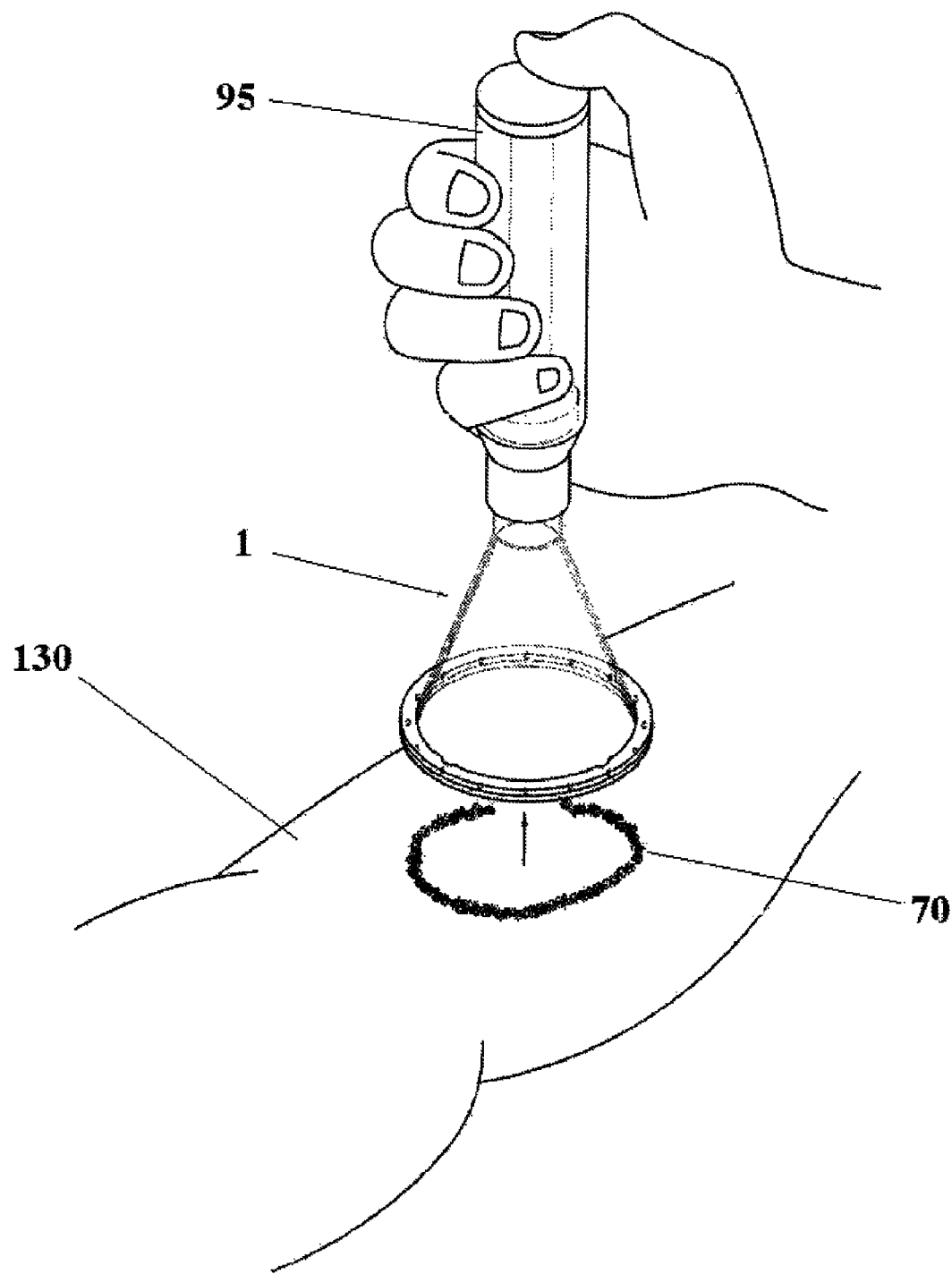
FIG. 7 displays the ink ring.

In the preferred embodiment, the foam ring 40 also has a small amount of skin marking dye 70 in it to leave a temporary ring stamp on the skin, demarcating the area of anesthesia as shown in FIG. 7.

In one embodiment, the conduits 60 are matched to the number of injection needles 50. In an alternative embodiment there is a lesser number of conduits 60 than injection needles 50 where the conduits feed to a ring-shaped manifold chamber 80 contiguous with the injection needles. In yet another possible embodiment, the body of the device is essentially just a cone within a cone that are spaced very close together allowing the anesthetic to flow between the cones. Each of these aforementioned embodiments are merely a continuum of the same device of which only the number and the width of the conduits are variable. Each embodiment would assure equal amounts of anesthetic fed to each needle 50.

Although this device is demonstrated here primarily as something intended to be attached to a Luer-Lock syringe 100, this does not exclude the potential to be utilized as part of a device that has a self-contained sealed ampule 95 of anesthetic 120 thus requiring no additional syringe or supplies as displayed in FIG. 7. In this alternative embodiment, the one-time-use device 1 with the self-contained sealed ampule 95 of anesthetic 120 would be even more time efficient and allow for even greater ease of use for emergent surgical procedures.

Also, the base 30 can be elliptical shape or can be a triangle or a square or a rectangular shape.

As to a further discussion of the manner of usage and operation of the present invention, the same should be apparent from the above description. Accordingly, no further discussion relating to the manner of usage and operation will be provided.

With respect to the above description, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A device for local anesthesia injection comprising:
a cone having a distal end and a proximal end;
a base positioned on the distal end;
a chamber positioned on the proximal end;
said cone further comprising a flange with an opening peripherally connected to said chamber with a delivery device containing an anesthetic attached on top of said flange;
the cone further comprising a plurality of conduits that extend from said chamber to a plurality of needles with each said conduit connected to a single needle wherein said needles are circumferentially distributed evenly around a lower surface of the base and protrude from the base;
the cone further comprising a compressed rubber foam having a round or oblong shape attached to said base wherein said needles are buried in said foam and the length of the needle is dependent on the compressibility factor of the foam and wherein the foam contains a skin markable dye for placing a temporary ring stamp on the skin, demarcating the area of said anesthetic delivery.

2. A device according to claim 1 further comprising wherein said delivery device is a luer lock syringe said delivery device be a Luer lock syringe.

3. A device according to claim 1 further comprising wherein said delivery device is a self contained means attached to said chamber said delivery device being self contained means attached to said chamber.

4. A device according to claim 3 further comprising said self contained means is an Ampule.

5. A device for local anesthesia injection comprising:
a cone having a distal end and a proximal end;
a base positioned on the distal end;
a chamber positioned on the proximal end;
said cone further comprising a flange with an opening peripherally connected to said chamber with a delivery device containing an anesthetic attached on top of said flange;
the cone further comprising a plurality of conduits that extend from said chamber and connects to a ring shaped manifold chamber that connects to a plurality of needles wherein said needles are circumferentially distributed evenly around a lower surface of the base and protrude from the base;
the cone further comprising a compressed rubber foam having a round or oblong shape attached to said base where said needles are buried in said foam and the length of the needle is dependent on the compressibility factor of the foam and wherein the foam contains a skin markable dye for placing a temporary ring stamp on the skin, demarcating the area of said anesthetic delivery.

6. A device according to claim 5 further comprising wherein said delivery device is a luer lock syringe said delivery device be a Luer lock syringe.

7. A device according to claim 5 further comprising wherein said delivery device is a self contained means attached to said chamber said delivery device being self contained means attached to said chamber.

8. A device according to claim 7 further comprising having said self contained means is an Ampule.

* * * * *